United States Patent [19]

Mills

[11] Patent Number: 4,645,771
[45] Date of Patent: * Feb. 24, 1987

[54] TETRAHYDROPYRIDINE DERIVATIVES

[75] Inventor: Stuart D. Mills, Macclesfield, England

[73] Assignee: Imperial Chemical Industries PLC, London, England

[*] Notice: The portion of the term of this patent subsequent to May 12, 1998 has been disclaimed.

[21] Appl. No.: 428,822

[22] Filed: Sep. 30, 1982

Related U.S. Application Data

[63] Continuation of Ser. No. 26,234, Apr. 2, 1979, abandoned.

[30] Foreign Application Priority Data

Apr. 12, 1978 [GB] United Kingdom .............. 14323/78
Oct. 12, 1978 [GB] United Kingdom .............. 40272/78

[51] Int. Cl.$^4$ ............................................. A61K 31/44
[52] U.S. Cl. .................................. 514/277; 514/357; 546/329; 546/330; 546/333; 546/339; 546/340; 546/342; 546/343; 546/348; 546/346
[58] Field of Search .............. 546/329, 330, 333, 339, 546/340, 342, 343, 348, 346; 424/263; 514/277, 357

[56] References Cited

U.S. PATENT DOCUMENTS

| | | | |
|---|---|---|---|
| 2,609,270 | 9/1952 | Couper | 546/346 |
| 2,967,182 | 1/1961 | Pohland | 546/348 X |
| 3,125,488 | 3/1964 | Biel | 546/346 X |
| 3,284,457 | 11/1966 | Beschke et al. | 546/346 |
| 3,632,767 | 1/1972 | Gray et al. | 546/346 X |
| 3,758,483 | 9/1973 | Edenhofer | 546/346 X |
| 4,001,414 | 1/1977 | Jarque et al. | 546/343 X |
| 4,028,371 | 6/1977 | Jarque et al. | 546/343 |
| 4,225,602 | 9/1980 | Johnson et al. | 424/263 |
| 4,267,183 | 5/1981 | Johnson et al. | 424/263 |

FOREIGN PATENT DOCUMENTS

| | | | |
|---|---|---|---|
| 778383 | 2/1968 | Canada | 546/346 |
| 1445560 | 10/1969 | Fed. Rep. of Germany | 546/346 |
| 2101997 | 8/1972 | Fed. Rep. of Germany | 546/348 |
| 2101998 | 8/1972 | Fed. Rep. of Germany | |
| 754372 | 8/1956 | United Kingdom | 546/346 |

OTHER PUBLICATIONS

Petrow, et al., J. Pharm. Pharmacal., 1962, 14, pp. 306–314.
Podesta, et al., Eur. J. Med. Chem.–Chimica Therapeutica, 1974, 9, pp. 487–490.
Oediger, et al., Liebigs Ann. Chem., 784 (1972) pp. 21–27.

*Primary Examiner*—Joseph Paul Brust
*Attorney, Agent, or Firm*—Cushman, Darby & Cushman

[57] ABSTRACT

The disclosure concerns novel 1-benzyl-1,2,3,6-tetrahydropyridine derivatives of the formula:

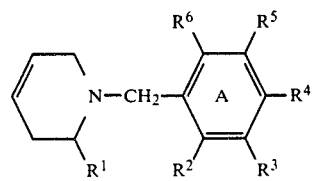

wherein $R^1$ is hydrogen or a (1–4C)-alkyl radical, and benzene ring A bears one or two substituents selected from combinations of halogeno, (1–4C)-alkyl, (1–4C)-alkoxy, hydroxy, nitro, cyano, carboxamido, carboxyl, [(1–4C)-alkoxy]carbonyl, hydroxymethylene, amino, (1–4C)-alkanoylamino, (1–4C)-alkylsulphonamido, [(1–4C)-alkoxy]carbonyloxy, (1–4C)-alkanoyloxy and optionally substituted benzoyloxy radicals, and their pharmaceutically acceptable salts; pharmaceutical compositions thereof; analogy processes for their manufacture; and methods of medical treatment employing such derivatives.

The compounds of formula I are inhibitors of the aggregation of blood platelets and are of application in the treatment or prophylaxis of thrombosis or occlusive vascular disease. Representative compounds possessing particularly good blood platelet aggregation inhibitory properties are 1-(3,4-dichloro-, 4-chloro-3-hydroxy-, and 4-hydroxy-benzyl)-1,2,3,6-tetrahydropyridine, preferably as their hydrochloride salts.

4 Claims, No Drawings

TETRAHYDROPYRIDINE DERIVATIVES

This is a continuation of application Ser. No. 026,234, filed Apr. 2, 1979, now abandoned.

This invention relates to novel pyridine derivatives and, more particularly, it relates to novel 1-benzyl-1,2,3,6-tetrahydropyridine derivatives which inhibit the aggregation of blood platelets.

It is known that various N-benzyl 4,5,6,7-tetrahydrothieno[3,2-c]pyridine and N-benzyl 4,5,6,7-tetrahydrofuran[3,2-c]pyridine derivatives possess anti-inflammatory and blood platelet aggregation inhibitory properties (M Podesta et alia, *European J. Medicinal Chemistry, Chimica Therapeutica*, 1974, 9, 487–490). We have now discovered that certain novel 1-benzyl-1,2,3,6-tetrahydropyridine derivatives of formula I specified hereinbelow unexpectedly also possess the property of inhibiting the aggregation of blood platelets, and this is the basis of our invention. A related compound, 1-benzyl-1,2,3,6-tetrahydropyridine, is known as a chemical intermediate (Petrow and Stephenson, *J. Pharm. Pharmacol.*, 1962, 14, 306–313). In addition, 1-(alkyl- or halogenobenzyl)-1-2,3,6-tetrahydropyridines are within the broad scope of the claims of West German Offenlegungschrift No. 2,101,998 (addressed to chemical intermediates) but are not specifically mentioned therein. All the compounds of formula I defined hereinbelow are believed to be both novel and unobvious over the known art.

According to the invention there is provided a 1-benzyl-1,2,3,6-tetrahydropyridine derivative of the formula:

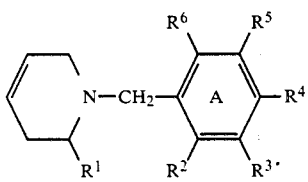

I wherein $R^1$ is hydrogen or a (1-4C)-alkyl radical; one of $R^2$, $R^3$, $R^4$, $R^5$ and $R^6$ is a halogeno, (1-4C)-alkyl, (1-4C)-alkoxy, hydroxy, nitro, cyano, carboxamido, carboxyl, [(1-4C)-alkoxy]carbonyl, hydroxymethylene, amino, (1-4C)-alkanoylamino, (1-4C)-alkylsulphonamido, [(1-4C)-alkoxy]carbonyloxy, (1-4C)-alkanoyloxy or an optionally substituted benzoyloxy radical, another of $R^2$, $R^3$, $R^4$, $R^5$ and $R^6$ is hydrogen, or a halogeno, hydroxy, nitro, (1-4C)-alkyl or (1-4C)-alkoxy radical, and the remainder of $R^2$, $R^3$, $R^4$, $R^5$ and $R^6$ is hydrogen; or two of $R^2$, $R^3$, $R^4$, $R^5$ and $R^6$ are both [(1-4C)-alkoxy]-carbonyloxy, (1-4C)-alkanoyloxy or optionally substituted benzoyloxy radicals; and the remainder of $R^2$, $R^3$, $R^4$, $R^5$ and $R^6$ is hydrogen; but benzene ring A is other than a 2-chlorophenyl radical when $R^1$ is hydrogen; or a pharmaceutically acceptable acid-addition salt thereof; or when one of $R^2$, $R^3$, $R^4$, $R^5$ and $R^6$ is a carboxy radical, a pharmaceutically acceptable base-addition salt thereof.

Within the above definition particular groups of compounds of the invention are comprised by the following compounds of formula I wherein:

(i) $R^2$ is a (1-4C)-alkyl, (1-4C)-alkoxy, halogeno, carboxamido, hydroxy, nitro or cyano radical, and $R^3$, $R^4$, $R^5$ and $R^6$ are hydrogen, but $R^2$ is other than a chloro radical when $R^1$ is hydrogen;

(ii) $R^3$ is a (1-4C)-alkyl or hydroxy radical, and $R^2$, $R^4$, $R^5$ and $R^6$ are hydrogen;

(iii) $R^4$ is a (1-4C)-alkyl, (1-4C)-alkoxy, halogeno, hydroxy, nitro, cyano, carboxamido, carboxy, [(1-4C)-alkoxy]carbonyl, hydroxymethylene, amino, (1-4C)-alkanoylamino, [(1-4C)-alkoxy]carbonyloxy, (1-4C)-alkylsulphonamido, (1-4C)-alkanoyloxy or an optionally substituted benzoyloxy radical; and $R^2$, $R^3$, $R^5$ and $R^6$ are hydrogen;

(iv) $R^5$ and $R^6$ are hydrogen, $R^2$ and $R^4$ independently, or $R^3$ and $R^4$ independently, are selected from (1-4C)-alkyl, (1-4C)-alkoxy, halogeno, hydroxy and nitro radicals, or are both (1-4C)-alkanoyloxy, [(1-4C)-alkoxy]carbonyloxy or optionally substituted benzoyloxy radicals, and $R^3$ or $R^2$ respectively is hydrogen; or (v) $R^2$ and $R^3$, $R^2$ and $R^5$, $R^2$ and $R^6$, or $R^3$ and $R^5$ are independently selected from (1-4C)-alkyl, halogeno and hydroxy radicals, or are both (1-4C)-alkanoyloxy, [(1-4C)-alkoxy]carbonyloxy or optionally substituted benzoyloxy radicals, and the remainder of $R^2$, $R^3$, $R^4$, $R^5$ and $R^6$ is hydrogen;

and in each group $R^1$ is hydrogen or a (1-4C)-alkyl radical, and together with the pharmaceutically acceptable acid- or base-addition salts thereof as set out above.

Particular values for the radicals $R^2$, $R^3$, $R^4$, $R^5$ and $R^6$ which are substituents on benzene ring A are by way of example only:

for a halogeno radical, a fluoro, chloro or bromo radical;

for a (1-4C)-alkyl radical, a methyl or ethyl radical;

for a (1-4C)-alkoxy radical, a methoxy or ethoxy radical;

for a [(1-4C)-alkoxy]carbonyl radical, a methoxycarbonyl or ethoxycarbonyl radical;

for a (1-4C)-alkanoylamino radical, an acetamido radical;

for a (1-4C)-alkylsulphonamido radical, a methyl sulphonamido radical;

for a [(1-4C)-alkoxy]carbonyloxy radical, a methoxycarbonyloxy or ethoxycarbonyloxy radical;

for a (1-4C)-alkanoyloxy radical, an acetoxy radical;

and for an optionally substituted benzoyloxy radical, a benzoyloxy, chlorobenzoyloxy or methylbenzoyloxy radical.

A particular value for $R^1$ when it is a (1-4C)-alkyl radical is, for example, a methyl radical.

A preferred value for $R^1$ is when it is hydrogen.

Specific combinations of $R^2$, $R^3$, $R^4$, $R^5$ and $R^6$ which are of interest are those wherein benzene ring A is a 2-fluoro-, 2-chloro-, 2-bromo-, 2-methyl-, 2-methoxy-, 2-nitro-, 2-cyano- or 2-carboxamido-phenyl radical; a 3-methyl- or 3-methoxy-phenyl radical; a 4-fluoro-, 4-chloro-, 4-bromo-, 4-methyl-, 4-methoxy-, 4-hydroxy, 4-nitro-, 4-cyano-, 4-carboxamido-, 4-carboxy-, 4-methoxycarbonyl-, 4-hydroxymethylene-, 4-amino-, 4-acetamido-, 4-methylsulphonamido-, 4-ethoxycarbonyloxy-, 4-acetoxy- or 4-benzoyloxy-phenyl radical; a 2-fluoro-4-chloro-, 2-chloro-4-fluoro-, 2-chloro-4-bromo-, 2,4-difluoro-, 2,4-dichloro-, 2-chloro-4-nitro-, 2-chloro-4-hydroxy- or 2-methyl-4-hydroxy-phenyl radical; a 2,3-dichloro- or 2-hydroxy-3-chloro-phenyl radical; a 2,5-dihydroxy-, 2,5-dimethyl- or 2,5-dichlorophenyl radical; a 2,6-dihydroxy-, 2,6-difluoro- or 2,6-dichlorophenyl radical; a 3,4-dichloro-, 3,4-dibromo-, 3,4-dihydroxy-, 3-chloro-4-bromo-, 3-bromo-4-chloro-, 3-chloro-4-methyl-, 3-methyl-4-chloro-, 3-hydroxy-4-chloro-, 3-chloro-4-hydroxy-, 3-methyl-4-hydroxy- or a 3-methoxy-4-hydroxy-phenyl radical; or a 3,5-dichlorophenyl radical.

Specific groups of compounds of the invention which are of particular interest are comprised by those compounds of formula I wherein:
(i) $R^2$ is hydrogen, a halogeno or (1–4C)-alkyl radical, $R^4$ is a halogeno, hydroxy or (1–4C)-alkylsulphonamido radical, and $R^3$, $R^5$ and $R^6$ are hydrogen;
(ii) $R^3$ is a halogeno, (1–4C)-alkyl, (1–4C)-alkoxy or hydroxy radical, $R^4$ is a halogeno or hydroxy radical, and $R^2$, $R^5$ and $R^6$ are hydrogen; or
(iii) $R^3$ and $R^5$, are the same or different halogeno radicals, and $R^2$, $R^4$ and $R^6$ are hydrogen; and in each group $R^1$ is hydrogen or a methyl radical, and together with the pharmaceutically acceptable acid-addition salts thereof.

Yet further groups of compounds of the invention which are especially preferred are comprised by those compounds of formula I wherein $R^2$, $R^3$, $R^4$, $R^5$ and $R^6$ have any of the sets of values specified in groups (i)–(iii) above and in addition $R^1$ is hydrogen, together with the pharmaceutically acceptable acid-addition salts thereof.

Specific compounds of the invention are mentioned in the accompanying Examples, but those of particular interest are as follows: 1-(3,4-dichlorobenzyl)-1,2,3,6-tetrahydropyridine, 1-(3,5-dichlorobenzyl)-1,2,3,6-tetrahydropyridine, 1-(3,4-dihydroxybenzyl)-1,2,3,6-tetrahydropyridine, 1-(4-hydroxybenzyl)-1,2,3,6-tetrahydropyridine, 1-(4-methylsulphonamidobenzyl)-1,2,3,6-tetrahydropyridine, 1-(2-chloro-4-hydroxybenzyl)-1,2,3,6-tetrahydropyridine, 1-(4-hydroxy-3-methylbenzyl)-1,2,3,6-tetrahydropyridine, 1-(4-hydroxy-3-methoxybenzyl)-1,2,3,6-tetrahydropyridine and 1-(4-chloro-3-hydroxybenzyl)-1,2,3,6-tetrahydropyridine; or a pharmaceutically acceptable acid-addition salt thereof.

Particular pharmaceutically acceptable acid-addition salts of compounds of formula I are, for example, salts with inorganic acids, for example hydrochloride, hydrobromide, sulphate or phosphate salts, or salts with organic acids affording a pharmaceutically acceptable anion, for example tartrate, citrate, lactate, fumarate, toluene-p-sulphonate or oxalate salts.

Particular pharmaceutically acceptable base-addition salts of compounds of formula I wherein $R^2$, $R^3$, $R^4$, $R^5$ or $R^6$ is a carboxy radical are, for example, salts with inorganic bases, for example sodium, potassium, aluminium, calcium or magnesium salts.

It will be recognised that those compounds of formula I wherein $R^1$ is a (1–4C)-alkyl radical possess an asymmetric carbon atom and as such may be isolated in a racemic and two optically active forms. It is to be understood that this specification is addressed to the racemic forms of such compounds of formula I and to those optically active forms which possess the above mentioned useful biological properties; it being well known in the art how to prepare the optically active forms by resolution or synthesis from optically active starting materials, and how to evaluate the biological activity of the individual isomers by standard tests, for example that mentioned hereinafter.

The compounds of formula I may be manufactured by any general process of organic chemistry known to be applicable to the synthesis of analogous compounds. Such processes are provided as a further feature of the invention and are illustrated by the following procedures in which $R^1$, $R^2$, $R^3$, $R^4$, $R^5$ and $R^6$ have any of the meanings defined hereinabove:

(a) For a compound of formula I wherein $R^2$, $R^3$, $R^4$, $R^5$ and $R^6$, are other than [(1–4C)-alkoxy]carbonyloxy, (1–4C)-alkanoyloxy or optionally substituted benzoyloxy radicals, a 1,2,3,6-tetrahydropyridine of the formula:

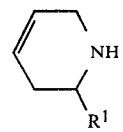

II is reacted with a benzyl halide of the formula:

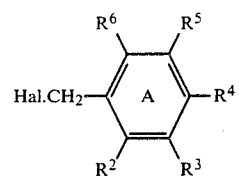

III wherein Hal, is a chlorine, bromine or iodine atom, and $R^2$, $R^3$, $R^4$, $R^5$ and $R^6$ are other than hydroxy radicals.

The process is conveniently carried out in the presence of a base, for example an alkali metal hydroxide or carbonate, for example sodium or potassium hydroxide or carbonate. Alternatively, an excess of the tetrahydropyridine of formula II may be used. The process is preferably performed in a suitable solvent or diluent, for example a (1–4C)-alkanol such as ethanol or propan-2-ol, at a temperature in the range, for example, 20° to 120° C.

The necessary starting materials may be made by conventional procedures well known in the art.

It will be appreciated that when a compound of formula I wherein $R^2$, $R^3$, $R^4$, $R^5$ or $R^6$ is a hydroxy radical is required, it is necessary to use a benzyl halide of formula III wherein the corresponding radical on benzene ring A is a [(1–4C)-alkoxy]carbonyloxy, (1–4C)-alkanoyloxy, or optionally substituted benzoyloxy radical, since hydroxybenzyl halides are highly unstable; it being further understood that hydrolysis of such acyloxy radicals will take place during the process (a) so that the compound isolated is that in which benzene ring A bears a hydroxy radical. Such a procedure is illustrated in Example 8 hereinafter.

(b) For a compound of formula I wherein none of $R^2$, $R^3$, $R^4$, $R^5$ and $R^6$ are [(1–4C)-alkoxy]carbonyloxy, (1–4C)-alkanoyloxy or optionally substituted benzoyloxy radicals, a quaternary salt of the formula:

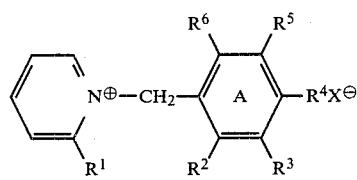

IV wherein $X^\ominus$ is an anion, for example a chloride bromide or iodide, is reduced with a suitable reducing agent.

A suitable reducing agent is, for example, an inorganic hydride reducing agent, for example sodium or potassium borohydride, sodium or lithium cyanoborohydride, aluminium hydride or lithium aluminium hydride. The process is conveniently carried out in an inert diluent or solvent, for example, tetrahydrofuran when an aluminium hydride is used as reducing agent, or for example a C_{1-4}-alkanol, for example ethanol, when a borohydride or cyanoborohydride is used as reducing agent. The process is preferably carried out at 5 or near room temperature, for example at 15°–35° C., when an inorganic hydride reducing agent is used.

Alternatively, a suitable reducing agent is, for example, a mixture of anhydrous sodium formate in formic, acid, and in which case an excess of formic acid may be used as diluent or solvent and the process is preferably carried out at a temperature in the range, for example, 100°–160° C. This reducing agent is particularly useful when benzene ring A bears a substituent which may be reduced by an inorganic hydride reducing agent, for example a [(1-4C)-alkoxy]carbonyl or carboxy radical.

The necessary starting materials of formula IV may be obtained by reacting pyridine or a 2-[(1-4C)-alkyl]-pyridine with a benzyl halide of the formula III, conveniently at an elevated temperature, for example at 50°–120° C., and optionally, in the presence of a suitable solvent or diluent, for example toluene, xylene, dioxan, acetonitrile or tetrahydrofuran. When a quaternary salt of formula IV wherein $X^{\ominus}$ is other than a halide anion is required, it may be obtained by conventional anion exchange procedures from the corresponding quaternary halide salt.

The quaternary salts of formula IV are conveniently made and used in situ.

It will be appreciated that when a compound of formula I wherein $R^2$, $R^3$, $R^4$, $R^5$ or $R^6$ is a hydroxy radical is required, it is necessary to use a quaternary salt of formula IV wherein the corresponding radical on benzene ring A is a [(1-4C)-alkoxy]carbonyloxy, (1-4C)-alkanoyloxy or optionally substituted benzoyloxy radical, for the reasons stated above in connection with process (a).

(c) For a compound of formula I wherein $R^2$, $R^3$, $R^4$, $R^5$ or $R^6$ is a halogeno, (1-4C)-alkyl, (1-4C)-alkoxy, hydroxy, hydroxymethyl or amino radical, an amide of the formula:

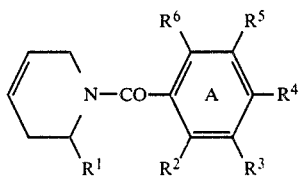

V wherein $R^2$, $R^3$, $R^4$, $R^5$ and $R^6$ have the meanings defined immediately above, or are nitro, carboxy or [(1-4C)-alkoxy]carbonyl radicals, is reduced with a complex aluminium hydride.

The process is preferably carried out in a suitable solvent or diluent, for example, tetrahydrofuran, diethyl ester, di-n-butyl ether or 1,2-dimethoxyethane, and a particularly suitable complex aluminium hydride is, for example lithium aluminium hydride. The process is conveniently carried out at, or near, room temperature, for example at 15°–35° C.

The starting materials of formula V may be obtained in an analogous manner and using similar conditions to those described in process (a) for compounds of formula I, except that an inert solvent or diluent is necessary, for example, n-butyl acetate, toluene, tetrahydrofuran, pyridine, chloroform or methylene dichloride, and a benzoyl halide of the formula:

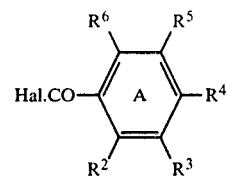

VI wherein Hal, is a chlorine or bromine atom and $R^2$, $R^3$, $R^4$, $R^5$ and $R^6$ have the meanings stated immediately above is used.

When a compound of formula I wherein $R^2$, $R^3$, $R^4$, $R^5$ or $R^6$ is an amino radical is required, the corresponding nitrobenzoyl halide of formula VI is employed, since reaction of the compound of formula V obtainable by the reaction with a tetrahydropyridine of formula II, in process (d) results in concomitant reduction of the nitro radical to an amino radical.

Similarly, when a compound of formula I wherein $R^2$, $R^3$, $R^4$, $R^5$ or $R^6$ is a hydroxymethylene radical is required, an amide of formula V wherein ring A bears a carboxy or (1-4C)-alkoxycarbonyl radical may be employed since these radicals are reduced to hydroxymethylene radicals by complex aluminium halides. The necessary carboxy amides of formula V may be obtained by hydrolysis of the corresponding [(1-4C)-alkoxy]carbonyl amides, for example using the conditions described hereinafter in process (f).

(d) A 1,2,3,6-tetrahydropyridine of the formula II is reacted with an aldehyde of the formula:

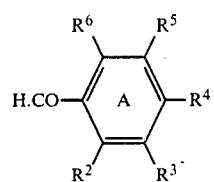

VII in the presence of a suitable reducing agent.

A suitable reducing agent is one which does not affect substituents which are present on benzene ring A of the aldehyde of formula VII. For example, an inorganic hydride, such as sodium or potassium borohydride, or lithium or sodium cyanoborohydride, may be employed. The process is conveniently carried out at a temperature in the range, for example, 15° to 30° C., and in a suitable solvent or diluent, for example ethanol or propan-2-ol.

The aldehydes of formula VII may be obtained by standard procedures of organic chemistry.

Process (d) is of the reaction type known as reductive amination and as such may proceed wholly or in part via an intermediate of the formula:

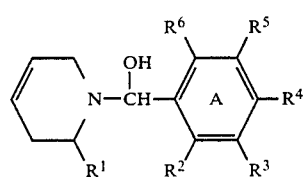

VIIa formed in situ and which is subsequently reduced. It is to be understood that this invention also embraces the separate reduction of an intermediate of formula VIIa produced, for example, by reacting a 1,2,3,6-tetrahydropyridine of formula II with an aldehyde of formula VII in the absence of a reducing agent.

(e) For a compound wherein $R^2$, $R^3$, $R^4$, $R^5$ or $R^6$ is a carboxy or carboxamido radical, a nitrile of the formula:

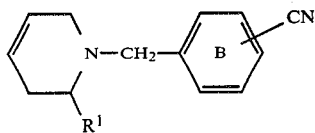

VIII wherein benzene ring B optionally bears a halogeno, hydroxy, [(1–4C)-alkoxy]carbonyloxy, (1–4C)-alkanoyloxy, optionally substituted benzoyloxy, nitro, (1–4C)-alkyl or (1–4C)-alkoxy radical, is hydrolysed.

It will be recognised that depending on the hydrolysis conditions used the cyano radical in the nitrile of formula VIII may be converted into a carboxamido or a carboxyl radical, or a mixture thereof may be obtained which can be separated by conventional procedures. It will also be recognised that an optional acyloxy radical such as a (1–4C)-alkanoyloxy radical, on benzene ring B in the nitrile of formula VIII will be converted to a hydroxy radical during process (e).

Suitable hydrolysis conditions are, for example, when an aqueous mineral acid, for example hydrochloric or hydrobromic acid, is employed at a temperature in the range, for example, 20°–100° C., conveniently in the presence of a suitable solvent or diluent, for example, ethanol, propan-2-ol or acetic acid. Formation of a carboxylic acid of formula I rather than a carboxamide is favoured by prolonged reaction at elevated temperature as illustrated in Examples 17 and 27 hereinafter.

Alternatively, suitable hydrolysis conditions are, for example, when an aqueous alkali metal hydroxide, for example sodium or potassium hydroxide, is employed at a temperature in the range, for example, 20°–100° C., conveniently in the presence of a suitable solvent or diluent, for example ethanol, propan-2-ol or ethylene glycol. Again, formation of a carboxylic acid (initially as its alkali metal salt) rather than a carboxamide is favoured by prolonged hydrolysis at an elevated temperature, for example at reflux temperature.

(f) For a compound of formula I wherein $R^2$, $R^3$, $R^4$, $R^5$ or $R^6$ is a hydroxy or amino radical, a compound of the formula:

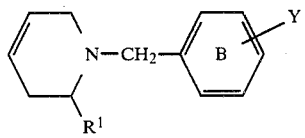

IX wherein benzene ring B optionally bears a halogeno, hydroxy, [(1–4C)-alkoxy]carbonyloxy, (1–4C)-alkanoyloxy, optionally substituted benzoyloxy, nitro, (1–4C)-alkyl or (1–4C)-alkoxy radical, and Y is a [(1–4C)-alkoxy]carbonyloxy, (1–4C)-alkanoyloxy, optionally substituted benzoyloxy, (1–4C)-alkanoylamino or (1–4C)-alkylsulphonamido radical, is hydrolysed.

Suitable hydrolysis conditions are, for example, when an aqueous mineral acid or an aqueous alkali metal hydroxide is employed, under conditions generally similar to those specified hereinabove for hydrolysis of nitriles in process (e). However, in general milder conditions are required for hydrolysis of the acyloxy radicals compared with those for the acylamino radicals. Thus, by way of example, whereas 1-(4-benzoyloxybenzyl)-1,2,3,6-tetrahydropyridine (IX, $R^1$=H, Y=4-PhCO.O) is hydrolysed by aqueous ethanolic sodium hydroxide at 20°–25° C., by contrast the hydrolysis of 1-(4-acetamidobenzyl)-1,2,3,6-tetrahydropyridine (IX, $R^1$=H, Y=4-AcNH) requires aqueous ethanolic potassium hydroxide for several hours at reflux temperature (see Examples 26 and 23 respectively, hereinafter).

It will be understood that when an acyloxy radical, such as a (1–4C)-alkanoyloxy radical, is present on benzene ring B in the compound of formula IX then this will be converted to a hydroxy radical during process (f).

(g) For a compound of formula I wherein $R^2$, $R^3$, $R^4$, $R^5$ or $R^6$ is a hydroxymethylene radical, a compound of the formula:

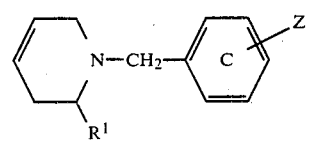

X wherein benzene ring C optionally bears a halogeno, hydroxy, (1–4C)-alkyl or (1–4C)-alkoxy radical, and Z is a carboxy or [(1–4C)-alkoxy]carbonyl radical, is reduced with a complex aluminium hydride.

A suitable complex aluminium hydride is for example lithium aluminium hydride, and suitable reaction conditions are, for example, those specified for process (c) hereinabove.

Whereafter, when a compound of formula I wherein $R^2$, $R^3$, $R^4$, $R^5$ or $R^6$ is a [(1–4C)-alkoxy]carbonyloxy, (1–4C)-alkanoyloxy or an optionally substituted benzoyloxy radical is required, the corresponding compound of formula I wherein $R^2$, $R^3$, $R^4$, $R^5$ or $R^6$ is a hydroxy radical is acylated by a conventional known procedure, for example by reaction, respectively, with the corresponding [(1–4C)-alkoxy]carbonyl, (1–4C)-alkanoyl or optionally substituted benzoyl halide, for example the chloride, as illustrated in Examples 22 and 61 hereinafter. Alternatively, the corresponding acid anhydride may be used as illustrated in Example 9 hereinafter. When a compound of formula I wherein benzene ring A bears two hydroxy radicals is acylated, one or both hydroxy radicals may be acylated depending on the quantity of acylating agent employed.

Whereafter, when a compound of formula I wherein $R^2$, $R^3$, $R^4$, $R^5$ or $R^6$ is a [(1–4C)-alkoxy]carbonyl radical is required the corresponding carboxylic acid of formula I wherein $R^2$, $R^3$, $R^4$, $R^5$ or $R^6$ is a carboxy radical is esterified by a conventional known procedure, for example by reaction with the appropriate (1–4C)-alkanol in the presence of an acid such as hydrogen chloride, as illustrated in Example 15 hereinafter.

Whereafter, when a pharmaceutically acceptable base-addition salt of a compound of formula I wherein $R^2$, $R^3$, $R^4$, $R^5$ or $R^6$ is a carboxy radical is required, such a compound of formula I is reacted with a suitable base using conventional procedures; and when a pharmaceutically acceptable acid-addition salt is required, a compound of formula I is reacted with a suitable acid using conventional procedures, such as those illustrated in the accompanying Examples.

The compounds of the invention are preferably isolated and used in the form of their acid-addition salts.

As stated above the compounds of formula I possess the property of inhibiting the aggregation of blood platelets. This property may be demonstrated in vivo using standard tests in laboratory animals, for example, in the following test in rabbits.

In this test blood samples are taken by a standard open flow technique from the central ear artery of rabbits. The samples are taken into a 3.8% w/v solution of trisodium citrate as anticoagulant and then centrifuged first at 150 g., and then at 1000 g., to prepare platelet rich and platelet poor plasma fractions, which are used to calibrate an instrument for measuring light transmittance and thus the amount of platelet aggregation. The extent of platelet aggregation following addition of adenosine 5'-diphosphate (ADP) (final concentration 0.5, 1.0, 2.0, 4.0 or 8.0 μM) to the platelet rich plasma fraction is then determined, and the value of maximum aggregation in response to each concentration of ADP is recorded. The rabbits are then dosed orally with test compound, and arterial blood samples are withdrawn at intervals after dosing. The platelet rich plasma fraction is prepared and ADP is added as above, and the extent of aggregation assessed by measuring the light transmittance of the sample. This value is compared with that obtained from the same rabbit before doing, so that a measure of the extent of inhibition of ADP induced blood platelet aggregation is obtained. By way of example only, the compound 1-(4-methylbenzyl)-1,2,3,6-tetrahydropyridine showed 62% inhibition of ADP-induced aggregation of blood platelets two hours after an oral dose (as its hydrochloride) of 100 mg./kg.

In general compounds of formula I produce significant inhibition of platelet aggregation in the above test at oral doses of 100 mg./kg. or less, without any signs of overt toxicity at the active dose.

Compounds which inhibit the aggregation of blood platelets, for example acetylsalicylic acid and ticlopidine, have been used in the treatment or prophylaxis of thrombosis or occlusive vascular disease, and it is envisaged that the compounds of the present invention will be used in a generally similar manner, and for the same clinical indications.

When used to inhibit the aggregation of blood platelets in warm-blooded animals including man, a compound of formula I may be administered at a daily oral dose in the range 1-30 mg./kg. and preferably in the range 1-10 mg./kg., or an equivalent amount of a pharmaceutically acceptable salt thereof. In man these doses are equivalent to daily oral doses of approximately 0.07-2.1 g. and 0.07-0.7 g. respectively, or an equivalent amount of a pharmaceutically acceptable salt.

The compounds of formula I are preferably administered in the form of pharmaceutical compositions, and according to a further feature of the invention there is provided a pharmaceutical composition which comprises a compound of formula I, or a pharmaceutically acceptable salt thereof as defined hereinbefore, together with a pharmaceutically acceptable diluent or carrier. Such a composition is conveniently in a form suitable for oral administration, for example as a tablet, capsule, aqueous or oily suspension, syrup or elixir. Alternatively it may be in a form suitable for parenteral administration by infusion or injection, for example as a sterile injectable solution or suspension, or in a form suitable for rectal administration, for example as a suppository.

Such compositions may be obtained by conventional procedures and using conventional excipients. A composition for oral administration should preferably contain from 5-500 mg. of active ingredient per unit dose, a composition for parenteral administration, 0.5-20 mg./ml. of active ingredient, and a composition for rectal administration, 50-500 mg. of active ingredient.

A composition of the invention may also conveniently contain one or more agents which can have a beneficial effect on thrombosis or occlusive vascular disease, or on associated conditions, selected from, for example, clofibrate, sulfinpyrazone, dipyridamole and methyl 4-(aminoacetyl)phenoxyacetate (or a salt thereof).

The invention is illustrated by the following Examples in which (i), yields are by way of example only and are not to be construed as the maximum attainable; (ii), evaporations were carried out in vacuo to dryness where possible, using a rotary evaporator; and (iii), melting points were determined in sealed glass capillary tubes:

EXAMPLE 1

1,2,3,6-Tetrahydropyridine (5.0 g.) was added to a mixture of 2-cyanobenzyl bromide (11.8 g.) and potassium carbonate (9.16 g.) in ethanol (80 ml.). The mixture obtained was heated under reflux for 2.5 hours, cooled and evaporated. Water (120 ml.) was added to the residue and the oily mixture obtained was extracted with ether (3×50 ml.). The combined extracts were washed with water, dried (MgSO$_4$) and evaporated. The residue oil was dissolved in toluene (20 ml.) to give a solution, which was treated with a slight excess of methanolic hydrogen chloride. The mixture was evaporated and the solid residue which was left was triturated with acetone, collected by filtration, and recrystallised from a mixture of ethanol and ethyl acetate to give 1-(2-cyanobenzyl)-1,2,3,6-tetrahydropyridine hydrochloride, as colourless needles (7.1 g), m.p. 219°-221° C.

EXAMPLES 2-6

Using a similar procedure to that described in Example 1, but using the appropriate substituted benzyl chloride or bromide of formula III, the following compounds of formula I may be obtained in yields of 60-80% as their hydrochloride salts:

| Example | Substituent on benzene ring A | m.p. (°C.) | Recrystallisation solvents |
| --- | --- | --- | --- |
| 2 | 4-methyl | 232-233 | i-PrOH/EtOAc |
| 3 | 2-fluoro | 179-180 | i-PrOH/EtOAc |
| 4 | 2-nitro | 178-181 | EtOH/Me$_2$CO |
| 5 | 4-methoxy | 203-204 | i-PrOH/EtOAc |
| 6 | 3-methyl | 191-192 | EtOH/Me$_2$CO |

EXAMPLE 7

A mixture of 4-hydroxybenzaldehyde (6.1 g.) and 1,2,3,6-tetrahydropyridine (8.3 g.) in methanol (70 ml.) was adjusted to pH7 by addition of ethereal hydrogen chloride. Sodium cyanoborohydride (3.15 g.) was then added in portions to the stirred solution at 25° C. The mixture was stirred at 20°-25° C. for four days, evaporated, and water (100 ml.) added to the resultant residue. The mixture obtained was adjusted to pH2 with dilute hydrochloric acid and extracted with ether (2×50 ml.). The extracts were discarded. The aqueous phase was separated and adjusted to pH9 with 10% w/v sodium carbonate solution, to give crude 1-(4-hydroxybenzyl)-1,2,3,6-tetrahydropyridine as a solid. This solid was dissolved in acetone (100 ml.) and the solution acidified to pH2 with ethereal hydrogen chloride to give 1-(4-hydroxybenzyl)-1,2,3,6-tetrahydropyridine hydrochloride (6.7 g.), m.p. 234°–236° C. (after recrystallisation from methanol/ethyl acetate.)

EXAMPLE 8

N-Bromosuccinimide (60.0 g.) was added in portions during 40 minutes to a solution of 4-acetoxytoluene (50.0 g.) and 2,2′-azobis(2-methylpropionitrile) (10 mg.) in carbon tetrachloride (300 ml.) heated under reflux and illuminated by a high energy tungsten lamp (275 watt). Heating and illumination were continuted for 80 minutes after the addition was complete. The mixture was then cooled and filtered. The solid residue was washed with carbon tetrachloride (100 ml.) and the combined filtrate and washings were evaporated to give 4-acetoxybenzyl bromide as a syrupy solid, which was dissolved, without further purification, in ethanol (300 ml.). 1,2,3,6-Tetrahydropyridine (83.0 g.) was then added to the solution during 10 minutes. The subsequent mixture was left at 20°–25° C. for 16 hours, and then evaporated. Water (300 ml.) was added to the residue obtained and the subsequent mixture was acidified to pH2 with dilute hydrochloric acid, and then extracted with ether (2×100 ml.) and the extracts discarded. The aqueous phase was basified to pH9 (sodium hydroxide solution) and extracted with ether (3×100 ml.). The extracts were washed with water (2×50 ml.), dried (MgSO4) and evaporated. The residue was dissolved in acetone (200 ml.), the solution obtained was filtered, and the filtrate acidified to pH2 with ethereal hydrogen chloride. There was thus obtained 1-(4-hydroxybenzyl)-1,2,3,6-tetrahydropyridine hydrochloride which was recrystallised from methanol/ethyl acetate to give pure material (34.6 g.), m.p. 234°–236° C.

EXAMPLE 9

A mixture of 1-(4-hydroxybenzyl)-1,2,3,6-tetrahydropyridine hydrochloride (1.0 g.), pyridine (7 ml.) and acetic anhydride (7 ml.) was kept at 20°–25° C. for 17 hours. The solid which formed was collected and washed with ether (50 ml.) to yield 1-(4-acetoxybenzyl)-1,2,3,6-tetrahydropyridine hydrochloride (1.1 g.), m.p. 220°–222° C.

EXAMPLE 10

Using a similar procedure to that described in Example 7 but starting from 2-hydroxybenzaldehyde (6.1 g.) and 1,2,3,6-tetrahydropyridine (8.3 g.) there was obtained 1-(2-hydroxybenzyl)-1,2,3,6-tetrahydropyridine as the free base (3.4 g.) (by basification of the acidified and extracted aqueous reaction mixture), which was an oil b.p. 100° C. (0.15 mmHg); microanalysis, $C_{12}H_{15}NO$ requires: C, 76.2; H, 7.9; N, 7.4; found C, 76.5, H, 8.2; N, 7.5%

NMR: [100 MHz in $d_6$-DMSO relative to TMS as internal standard]: δppm, 3.6 (2H, s); 4.72 (2H, q); 6.32 (1H, d); 6.55 (2H, d).

EXAMPLE 11

Using a similar procedure to that described in Example 7, but starting from 3,4-diacetoxybenzaldehyde (18.6 g.) and 1,2,3,6-tetrahydropyridine (13.9 g.) in methanol (150 ml.), there was obtained 1-(3,4-dihydroxybenzyl)-1,2,3,6-tetrahydropyridine as the free base (0.45 g.), m.p. >300° C.; microanalysis, $C_{12}H_{15}NO_2.0.25H_2O$ requires: C, 68.7; H, 7.4, N, 6.7%; found: C, 68.7; H, 6.6; N, 6.6%;

NMR: $d_6$DMSO, 60 MHz: δppm, 3.8 (2H, s), 5.75 (2H, m); 6.55 (3H, m); by basification of the acidified and ether extracted aqueous reaction mixture, followed by extraction with methylene chloride, evaporation of the dried extracts and recrystallisation of the resultant residue from methanol/acetone.

EXAMPLE 12

A solution of 1-(3-chloro-4-hydroxybenzoyl)-1,2,3,6-tetrahydropyridine (13.6 g.) in hot, dry tetrahydrofuran (300 ml.) was added slowly to a stirred suspension of lithium aluminium hydride (5.44 g.) in dry tetrahydrofuran (100 ml.). The mixture was heated under reflux for 17 hours and then cooled. Water (5.5 ml.), 15% w/v aqueous sodium hydroxide solution (5.5 ml.) and water (15 ml.) were added successively and the mixture was stirred for 1 hour and then filtered. The filtrate was evaporated and water (100 ml.) added to the residue. The mixture was filtered and the filtrate was acidified to pH2 with concentrated hydrochloric acid, and cooled to 5° C. The crystalline precipitate which formed was separated, washed with water (20 ml.), then with acetone (20 ml.), and recrystallised from methanol-acetone to give 1-(3-chloro-4-hydroxybenzyl)-1,2,3,6-tetrahydropyridine hydrochloride (6.6 g.), m.p. 225°–231° C.

The starting material was obtained as follows:

3-Chloro-4-hydroxybenzoic acid hemihydrate (14.5 g.) was heated under reflux for 1 hour with thionyl chloride (80 ml.). The mixture was then evaporated, the residue dissolved in ether and the subsequent solution evaporated. The residue obtained (3-chloro-4-hydroxybenzoyl chloride) was dissolved in ether (80 ml.). The stirred solution was then treated dropwise with a solution of 1,2,3,6-tetrahydropyridine (16.6 g.) in ether (50 ml.) with ice-cooling. The mixture was stirred for 17 hours and evaporated. Water (150 ml.) was then added and the mixture was stirred with ether (50 ml.). The insoluble material was separated by filtration, and combined with the solid obtained by basification of the aqueous phase. The combined solids were stirred with acetone (150 ml.), separated by filtration, washed with acetone (50 ml.) and air-dried to give 1-(3-chloro-4-hydroxybenzoyl)-1,2,3,6-tetrahydropyridine (13.6 g.), m.p. 186°–189° C.

EXAMPLES 13–14

Using a similar procedure to that described in Example 1 but starting with the appropriate benzyl bromide there were obtained in yields of 65–80%:

1-(3,4-dichlorobenzyl)-1,2,3,6-tetrahydropyridine (Example 13), m.p. 247°–250° C., after recrystallisation from isopropanol/ether; and 1-(3,5-dichlorobenzyl)-1,2,3,6-tetrahydropyridine (Example 14), m.p. 231°–234° C., after recrystallisation from methanol/ethyl acetate.

EXAMPLE 15

A suspension of 1-(4-carboxybenzyl)-1,2,3,6-tetrahydropyridine (1.5 g.) in methanolic hydrogen chloride (30 ml. of 20% w/w) was stirred for 17 hours at 25° C. The mixture was evaporated. 3N Sodium hydroxide solution (20 ml.) was added to the residue and the mixture obtained was extracted with ether (3×20 ml.). The aqueous phase was discarded and the ethereal extracts were combined, dried (MgSO$_4$) and acidified with ethereal hydrogen chloride to give 1-(4-methoxycarbonylbenzyl)-1,2,3,6-tetrahydropyridine hydrochloride (1.0 g.), m.p. 224°–226° C. (after recrystallisation from methanol/ether.)

EXAMPLE 16

Using a similar procedure to that described in Example 1, but starting from 4-cyanobenzyl bromide (19.5 g.) and 1,2,3,6-tetrahydropyridine (8.3 g.), there was obtained 1-(4-cyanobenzyl)-1,2,3,6-tetrahydropyridine hydrochloride (12.0 g.), m.p. 259°–261° C. after recrystallisation from a mixture of ethanol, methanol and acetone.

EXAMPLE 17

A solution of 1-(4-cyanobenzyl)-1,2,3,6-tetrahydropyridine hydrochloride (5.0 g.) in concentrated hydrochloric acid (100 ml.) was heated under reflux for 17 hours and evaporated. The residue was dissolved in acetone and evaporated three times to give crude 1-(4-carboxybenzyl)-1,2,3,6-tetrahydropyridine hydrochloride. Material of satisfactory analytical purity was obtained by dissolving the crude hydrochloride in 5% w/v sodium carbonate solution, extracting the solution with ethyl acetate, discarding the extracts and carefully acidifying the aqueous carbonate phase to liberate 1-(4-carboxybenzyl)-1,2,3,6-tetrahydropyridine.

EXAMPLES 18–21

Aqueous hydrobromic acid (48% w/w) was added dropwise, with stirring, to a solution of 1-(4-hydroxybenzyl)-1,2,3,6-tetrahydropyridine (4.0 g.) in acetone (50 ml.) until no further precipitate was obtained. The solid was collected by filtration and recrystallised from ethanol to give 1-(4-hydroxybenzyl)-1,2,3,6-tetrahydropyridine hydrobromide (Example 18) (2.9 g.), m.p. 187°–190° C.

Using an analogous procedure the following salts were obtained:

(i) from 1-(4-hydroxybenzyl)-1,2,3,6-tetrahydropyridine (2.0 g.) and concentrated sulphuric acid, 1-(4-hydroxybenzyl)-1,2,3,6-tetrahydropyridine sulphate (Example 19) (1.2 g.), m.p. 197°–201° C., after recrystallisation from ethanol;

(ii) from 1-(4-hydroxybenzyl)-1,2,3,6-tetrahydropyridine (3.0 g.) and toluene-p-sulphonic acid, 1-(4-hydroxybenzyl)-1,2,3,6-tetrahydropyridine toluene-p-sulphonate (Example 20) (2.4 g.), m.p. 105°–108° C., after recrystallisation from acetone; and (iii) from 1-(4-hydroxybenzyl)-1,2,3,6-tetrahydropyridine (2.0 g.) and fumaric acid adjusted to pH5, 1-(4-hydroxybenzyl)-1,2,3,6-tetrahydropyridine fumarate (Example 21) (2.0 g.), m.p. 197°–201° C. after recrystallisation from a mixture of methanol and acetone.

EXAMPLE 22

Benzoyl chloride (3.0 g.) was added to a vigorously stirred mixture of 1-(4-hydroxybenzyl)-1,2,3,6-tetrahydropyridine (4.0 g.) in N-sodium hydroxide solution (22 ml.) and ether (30 ml.). The mixture was stirred for 2 hours after the addition and then 3N-sodium hydroxide solution added to pH10. The subsequent mixture was extracted into ethyl acetate (2×30 ml.) and the combined extracts were dried (MgSO$_4$) and evaporated. The residue was dissolved in acetone (50 ml.) and the solution was treated with concentrated hydrochloric acid to pH2. The solid which precipitated was collected by filtration and recrystallised from isopropanol to give 1-(4-benzoyloxybenzyl)-1,2,3,6-tetrahydropyridine (1.8 g.), m.p. 220°–227° C.

EXAMPLE 23

1-(4-Acetamidobenzyl)-1,2,3,6-tetrahydropyridine (2.0 g.) was added to a solution of potassium hydroxide (3.0 g.) in ethanol (30 ml.) and water (5 ml.). The mixture was heated under reflux for 7 hours, and then concentrated to low volume in vacuo. Water (30 ml.) was added to the residue. The mixture obtained was extracted with ether (3×30 ml.) and the combined extracts were dried (MgSO$_4$) and acidified with ethereal hydrogen chloride to give a semi solid which crystallised on trituration with isopropanol. Recrystallisation from a mixture of methanol and ethyl acetate gave 1-(4-aminobenzyl)-1,2,3,6-tetrahydropyridine hydrochloride (1.1 g.), m.p. 212°–215° C.

EXAMPLE 24

4-Acetoxybenzyl bromide (3 g.) and pyridine (2.2 g.) were heated in acetone (25 ml.) under reflux for 3 hours. The solvent was removed by decantation and the residue was triturated with dioxan to give 4-(acetoxybenzyl)pyridinium bromide as a hygroscopic solid (5.1 g.). This solid was dissolved in ethanol (60 ml.), and was treated with sodium borohydride (2.95 g.). The subsequent mixture was stirred at 25° C. for 24 hours and then concentrated to low volume in vacuo. The residue was diluted with water (50 ml.) and then acidified to pH2 with 2N hydrochloric acid, and stirred for 20 minutes. 5% w/v Sodium carbonate solution was added to pH9 and the solid which precipitated was collected by filtration and stirred with acetone.

The solution obtained was separated by filtration and the filtrate was acidified with concentrated hydrochloric acid to give a precipitate of 1-(4-hydroxybenzyl)-1,2,3,6-tetrahydropyridine hydrochloride (0.4 g.) m.p. 234°–236° C.

EXAMPLE 25

1-(4-Hydroxybenzoyl)-1,2,3,6-tetrahydropyridine (5.0 g.) was added portionwise to a stirred suspension of lithium aluminium hydride (3 g.) in tetrahydrofuran (100 ml.) with occasional ice-cooling. The mixture was heated under reflux for 3 hours, cooled with ice-water and then water (3 ml.) cautiously added followed by 15% sodium hydroxide solution (3 ml.) and water (9 ml.). The mixture obtained was separated by filtration and the filtrate evaporated. The residue was dissolved in acetone and the solution dried (MgSO$_4$) and acidified with ethereal hydrogen chloride to give, a precipitate of 1-(4-hydroxybenzyl)-1,2,3,6-tetrahydropyridine hydrochloride (0.7 g.), m.p. 233°–235° C. The starting material was obtained as follows:

4-Hydroxybenzoic acid (11.04 g.) was heated under reflux with thionyl chloride (80 ml.) containing dimethylformamide (0.1 ml.) for 2 hours. The solution obtained was evaporated. The residue was dissolved in toluene and the subsequent solution was evaporated. The residue obtained (which contained 4-hydroxybenzoyl chloride) was dissolved in methylene chloride (80 ml.). The solution obtained was treated dropwise with 1,2,3,6-tetrahydropyridine to pH7 with stirring and ice-cooling. The mixture was further stirred at 25° C. after the addition was complete for 2 hours and then evaporated. The residue was stirred with water and the solid was collected by filtration and then washed with water and acetone. After recrystallisation from a mixture of ethanol and ethyl acetate, there was obtained 1-(4-hydroxybenzoyl)-1,2,3,6-tetrahydropyridine (11.3 g.), m.p. 202°–206° C.

EXAMPLE 26

A solution of 1-(4-benzoyloxybenzyl)-1,2,3,6-tetrahydropyridine (1.0 g.) in ethanol (15 ml.) and water (5 ml.) containing sodium hydroxide (0.245 g.) was stirred for 2.5 hours. Ice-water (35 ml.) was added followed by acetic acid to pH7. The solid which formed was collected by filtration, washed with water, dried and dissolved in acetone (10 ml.). The solution obtained was acidified with concentrated hydrochloric acid to pH3 to give 1-(4-hydroxybenzyl)-1,2,3,6-tetrahydropyridine hydrochloride (0.6 g.), m.p. 232°–4° C.

EXAMPLE 27

A solution of 1-(2-cyanobenzyl)-1,2,3,6-tetrahydropyridine (1 g.) in concentrated hydrochloric acid (5 ml.) was maintained at 25° C. for 3 hours, heated at 100° C. for 30 minutes, and then concentrated to low volume in vacuo. The residue was mixed with water (10 ml.) and the pH was adjusted to pH9 by addition of 5% w/v sodium carbonate solution. The mixture obtained was extracted with ether (2×10 ml.). The combined extracts were dried (MgSO$_4$) and acidified with ethereal hydrogen chloride to give a gum which solidified on trituration with ether and then acetone to give 1-(2-carboxamidobenzyl)-1,2,3,6-tetrahydropyridine hydrochloride (0.35 g.), m.p. 196°–198° C.

EXAMPLES 28–52

Using a similar procedure to that described in Example 1 but using the appropriate substituted benzyl chloride or bromide of the formula III (wherein R$^1$=H unless otherwise stated) the following compounds of formula I (R$^1$=H unless otherwise stated) were obtained as their hydrochloride salts:

| Example | Substituent(s) on benzene ring A | Yield (%) | m.p. (°C.) | Recrystallisation solvent(s) |
|---|---|---|---|---|
| 28 | 3-bromo-4-chloro | 34 | 245–246 | EtOH/MeOH/Et$_2$O |
| 29 | 3,4-dibromo | 52 | 249–251 | EtOH/MeOH/EtOAc |
| 30 | 4-bromo | 53 | 241–243 | EtOH/EtOAc |
| 31 | 4-nitro | 37 | 207–210 | i-PrOH/Et$_2$O |
| 32 | 4-chloro | 13 | 240–242 | i-PrOH/EtOAc |
| 33 | 2-fluoro-4-chloro | 56 | 206–209 | MeOH/EtOAc |
| 34 | 2-bromo | 46 | 196–201 | EtOH/Me$_2$CO |
| 35 | 2-chloro (R1 = methyl) | 56 | oil | Note (a) |
| 36 | 2-chloro-4-fluoro | 49 | 203–213 | EtOH/Me$_2$CO |
| 37 | 2-methoxy | 10 | 138–142 | Me.CO.Et |
| 38 | 2,3-dichloro | 32 | 186–188 | i-PrOH/EtOAc |
| 39 | 3-chloro-4-methyl | 62 | 230–235 | MeOH/EtOAc |
| 40 | 3-chloro-4-bromo | 60 | 246–252 | 2N-HCl |
| 41 | 2,6-di-hydroxy* | 17 | 187–189 | i-PrOH |
| 42 | 4-methyl-sulphonamido | 26 | 198–201 | EtOH |
| 43 | 2,6-dichloro | 22 | 174–176 | EtOH/Me$_2$CO |
| 44 | 2-chloro-4-bromo | 19 | 191–193 | EtOH/EtOAc |
| 45 | 2,5-dimethyl | 50 | 220–233 | i-PrOH/Et$_2$O |
| 46 | 2,6-di-fluoro | 19 | 187–188 | EtOH/EtOAc |
| 47 | 2-methyl | 52 | 186–189 | MeOH/EtOAc |
| 48 | 2,4-di-fluoro | 30 | 211–213 | EtOH/EtOAc |
| 49 | 3-methyl-4-chloro | 14 | 240–243 | — |
| 50 | 3-hydroxy-4-chloro* | 43 | 140–142 (free base) | Note (b) |
| 51 | 2-chloro-4-nitro | 30 | 197–199 | i-PrOH |
| 52 | 2-hydroxy-3-chloro* | 32 | 169–172 | i-PrOH |

*Starting materials for Example 41, 50 and 52 were 2,6-diacetoxybenzyl bromide, 3-acetoxy-4-chloro-benzyl bromide and 2-acetoxy-3-chlorobenzyl bromide respectively.

Note (a): isolated as the free base, having a satisfactory NMR (100 MHz, d$_6$-DMSO) : δ 1.05 (doublet, 3H), 3.65 (doublet, 2H), 5.61 (multiplet, 2H), 7.35 (multiplet, 4H). starting material: 2-methyl-1,2,3,6-tetrahydropyridine.

Note (b): purified as the free base by sublimation.

EXAMPLES 53–60

Using a similar procedure to that described in Example 7 but using the appropriate substituted aldehyde of formula VII (R$^1$=hydrogen), the following compounds of formula I (R$^1$=hydrogen) were obtained as their hydrochloride salts:

| Example | Substituent(s) on benzene ring A | Yield (%) | m.p. (°C.) | Recrystallisation solvent(s) |
|---|---|---|---|---|
| 53 | 4-fluoro | 17 | 220–221 | i-PrOH/EtOAc |
| 54 | 3-methyl-4-hydroxy | 66 | 192–194 | EtOh/Me$_2$CO |
| 55 | 3-methoxy-4-hydroxy | 13 | 188–189 | i-PrOH |
| 56 | 2-methyl-4-hydroxy | 63 | 181–184 | EtOH/Me$_2$CO |
| 57 | 4-acetamido* | 14 | 164–165 | Me$_2$CO |
| 58 | 2-chloro-4-hydroxy | 35 | 204–205 | EtOH |
| 59 | 2,5-di-hydroxy | 47 | 194–200 | EtOH/Me$_2$CO |
| 60 | 3-hydroxy | 38 | 144–146 | EtOH/Me$_2$CO |

*free base

EXAMPLE 61

Triethylamine (1.2 g.) was added with stirring to a solution of 1-(4-hydroxybenzyl)-1,2,3,6-tetrahydropyridine (1.9 g.) in methylene chloride (30 ml.) at 0° C. Ethyl chloroformate (1.2 g.) was then added dropwise and the mixture stirred at 25° C. for 16 hours and then evaporated. Water (30 ml.) was added to the residue and the mixture was extracted with ether (2×30 ml.). The combined extracts were dried (MgSO$_4$) and evaporated. The residue was dissolved in acetone (20 ml.) and acidified with ethereal hydrogen chloride to give 1-[4-(ethoxycarbonyloxy)benzyl]-1,2,3,6-tetrahydropyridine hydrochloride (1.5 g.) m.p. 168°–172° C. (after recrystallisation from ethanol-ethyl acetate).

EXAMPLE 62

1-(2,5-Dichlorobenzoyl)-1,2,3,6-tetrahydropyridine (10 g.) was reduced using a similar procedure to that described in Example 25 to give after recrystallisation from a mixture of isopropyl alcohol, methanol and ether, 1-(2,5-dichlorobenzyl)-1,2,3,6-tetrahydropyridine hydrochloride (2.4 g.), m.p. 221°–223° C.

The starting material was made from equivalent amounts of 1,2,3,6-tetrahydropyridine and 2,5-dichlorobenzyl chloride and had m.p. 91°–92° C.

EXAMPLE 63

1-(4-Carboxybenzyl)-1,2,3,6-tetrahydropyridine (3.0 g.) was added in portions to a stirred suspension of lithium aluminium hydride (1.2 g.) in dry tetrahydrofuran (60 ml.) cooled by an ice-bath. The mixture was then heated under reflux for 3 hours and cooled. Water (1.2 ml.) was added cautiously, followed by 3N sodium hydroxide solution (1.2 ml.) and then water (4.8 ml.). The solid which formed was removed by filtration and discarded. The filtrate was extracted with ether (100 ml.). The extract was washed with 3N sodium hydroxide solution (20 ml.), dried ($MgSO_4$), and then acidified with ethereal hydrogen chloride to give 1-(4-hydroxymethylbenzyl)-1,2,3,6-tetrahydropyridine hydrochloride (1.4 g.), m.p. 178°–180° C. (after recrystallisation from a mixture of ethanol and ethyl acetate).

EXAMPLE 64

Using a similar procedure to that described in Example 1, there was obtained 1-(2,4-dichlorobenzyl)-1,2,3,6-tetrahydropyridine hydrochloride in 16% yield, m.p. 175°–179° C., (recrystallised from isopropanol/ether).

EXAMPLE 65

Using a similar procedure to that described in Example 8 but replacing 1,2,3,6-tetrahydropyridine by 2-methyl-1,2,3,6-tetrahydropyridine, there was obtained 1-(4-hydroxybenzyl)-2-methyl-1,2,3,6-tetrahydropyridine as an oil which crystallised on stirring with petroleum ether (b.p. 60°–80° C.) to give the free base as a solid, m.p. 109°–112° C.

EXAMPLE 66 (Note: all parts are by weight)

A mixture of micro-crystalline cellulose (196 parts) and finely divided 1-(4-methylbenzyl)-1,2,3,6-tetrahydropyridine hydrochloride (200 parts) was sieved through a 30 mesh screen. Magnesium stearate (60 mesh particle size) (4 parts) was then added and, after thorough mixing, the mixture was compressed into tablets weighing 400 mg. and containing 200 mg. of active ingredient, which may be administered to man for therapeutic purposes.

Using a similar procedure, tablets containing 20, 50, 100 and 400 mg. of active ingredient may be obtained.

EXAMPLE 67

Using a similar procedure to that described in Example 66, there may be obtained tablets containing 20, 50, 100, 200 and 400 mg. of 1-(4-hydroxybenzyl)-1,2,3,6-tetrahydropyridine hydrochloride, suitable for administration to man for therapeutic purposes.

Alternatively the corresponding hydrobromide, sulphate, toluene p-sulphonate or fumarate salts described in Examples 18–21 respectively may be substituted for the above hydrochloride salt.

EXAMPLE 68

Using a similar procedure to that described in Example 66, there may be obtained tablets containing 20, 50, 100, 200 and 400 mg. of 1-(4-chloro-3-hydroxybenzyl)-1,2,3,6-tetrahydropyridine hydrochloride, or another compound of formula I as its pharmaceutically acceptable acid-addition salt (such as its hydrochloride) described in any one of Examples 1, 3–6, 9–17, 22–23, 27–49 and 51–65.

I claim:

1. A pharmaceutical composition for use in inhibiting the aggregation of blood platelets in a warm-blooded animal which comprises a therapeutically effective amount of a compound selected from the group consisting of a 1-benzyl-1,2,3,6-tetrahydropyridine derivative of the formula:

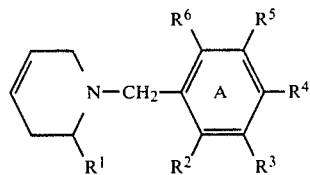

wherein $R^1$ is hydrogen or a methyl radical, $R^2$ is hydrogen, a halogeno or (1–4C)-alkyl radical, $R^4$ is a halogeno, hydroxy or (1–4C)-alkylsulphonamido radical, and $R^3$, $R^5$ and $R^6$ are hydrogen and the pharmaceutically acceptable acid-addition salts thereof; together with a pharmaceutically acceptable diluent or carrier.

2. A pharmaceutical composition for use in inhibiting the aggregation of blood platelets in a warm-blooded animal which comprises a therapeutically effective amount of a compound selected from the group consisting of a 1-benzyl-1,2,3,6-tetrahydropyridine derivative of the formula:

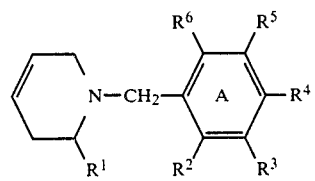

wherein $R^1$ is hydrogen or a methyl radical and benzene ring A is 4-chloro-, 4-fluoro-, 4-bromo-, 4-hydroxy-, 4-methylsulphonamido-, 2-fluoro-4-chloro-, 2-chloro-4-fluoro-, 2-chloro-4-bromo-, 2,4-difluoro-, 2,4-dichloro-, 2-chloro-4-hydroxy-, or 2-methyl-4-hydroxy-phenyl and the pharmaceutically acceptable acid-addition salts thereof; together with a pharmaceutically acceptable diluent or carrier.

3. The composition of claim 1 wherein the 1-benzyl-1,2,5,6-tetrahydropyridine is selected from the group consisting of
   1-(4-hydroxybenzyl)-1,2,3,6-tetrahyropyridine,
   1-(4-methylsulphonamidobenzyl)-1,2,3,6-tetrahydropyridine,
   1-(2-chloro-4-hydroxybenzyl)-1,2,3,6-tetrahydropyridine, and
   a pharmaceutically acceptable acid-addition salt thereof.

4. A composition according to claim 1 wherein said derivative is one wherein $R^1$, $R^2$, $R^3$, $R^5$ and $R^6$ are hydrogen and $R^4$ is chloro.

* * * * *